(12) United States Patent
Davies et al.

(10) Patent No.: US 10,309,920 B2
(45) Date of Patent: Jun. 4, 2019

(54) GATING SYSTEM AND METHOD FOR BIOSENSOR TEST STRIPS

(71) Applicant: Trividia Health, Inc., Fort Lauderdale, FL (US)

(72) Inventors: Stephen Davies, Coconut Creek, FL (US); Brent E. Modzelewski, Boca Raton, FL (US); Jeffrey Akins, Boca Raton, FL (US)

(73) Assignee: Trividia Health, Inc., Fort Lauderdale, FL (US)

( * ) Notice: Subject to any disclaimer, the term of this patent is extended or adjusted under 35 U.S.C. 154(b) by 61 days.

(21) Appl. No.: 15/606,441

(22) Filed: May 26, 2017

(65) Prior Publication Data

US 2017/0343504 A1 Nov. 30, 2017

Related U.S. Application Data

(60) Provisional application No. 62/341,759, filed on May 26, 2016.

(51) Int. Cl.
*G01N 27/327* (2006.01)

(52) U.S. Cl.
CPC ..... *G01N 27/3273* (2013.01); *G01N 27/3272* (2013.01)

(58) Field of Classification Search
CPC ..................................... G01N 27/327–27/3274
See application file for complete search history.

(56) References Cited

U.S. PATENT DOCUMENTS

| 5,526,120 A | 11/1996 | Jina et al. |
| 6,274,326 B1 | 8/2001 | Stoughton |
| 7,041,254 B2 | 5/2006 | Haviland et al. |
| 2008/0099332 A1 | 5/2008 | Scott et al. |
| 2014/0123735 A1 | 5/2014 | Uenosono et al. |
| 2014/0174953 A1 | 6/2014 | Elder et al. |

FOREIGN PATENT DOCUMENTS

| WO | 2010/126795 | 11/2010 |
| WO | 2015/100203 | 7/2015 |

OTHER PUBLICATIONS

International Search Report and Written Opinion for International Patent Application No. PCT/US17/34702, dated Aug. 15, 2017.

*Primary Examiner* — J. Christopher Ball
(74) *Attorney, Agent, or Firm* — Greenberg Traurig, LLP; David J. Dykeman; Roman Fayerberg

(57) ABSTRACT

A system is disclosed, the system comprises a diagnostic test strip having a diagnostic end and a meter contacting end, the meter contacting end having at least one identifying feature that distinguishes the meter contacting end from the diagnostic end; a diagnostic meter configured to read information from the meter contacting end of the test strip when the meter contacting end of the test strip is fully inserted in to the meter; and a port in the meter, the port having a gating mechanism configured to identify the meter contacting end and allow the test strip to be fully inserted into the meter only after the gating mechanism identifies the meter contacting end of the test strip as a proper end for insertion.

21 Claims, 19 Drawing Sheets

FIG. 18A
50
30
FIG. 18B
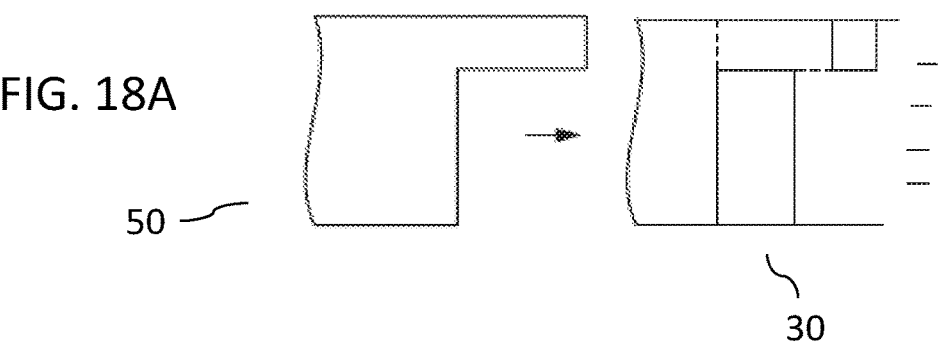
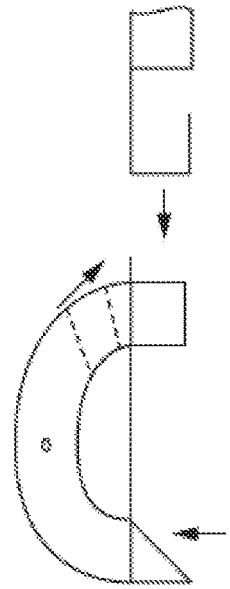

GATING SYSTEM AND METHOD FOR BIOSENSOR TEST STRIPS

CROSS REFERENCE TO RELATED APPLICATIONS

This application claims priority to and the benefit of U.S. provisional patent application No. 62/341,759, filed May 26, 2016, the entirety of which is incorporated herein by reference.

BACKGROUND

Field

The present invention relates to electrochemical test strips and, more particularly, to systems and methods for electrochemically sensing a particular constituent within a fluid through the use of diagnostic test strips.

Background

Many individuals and industries have a need to monitor the concentration of particular constituents in a fluid. The oil refining industry, wineries, and the dairy industry are examples of industries where fluid testing is routine. In the health care field, individuals such as diabetics, for example, have a need to monitor a particular constituent within their bodily fluids. A number of systems are available that allow people to test a body fluid, such as, blood, urine, or saliva, to conveniently monitor the level of a particular fluid analyte, such as, for example, cholesterol, proteins, or glucose. Such systems can include a test strip where the user applies a fluid sample and a reading device, hereafter called a meter, used with the test strip to determine the analyte level in the fluid sample.

Among the various technologies available for measuring liquid analyte levels, electrochemical amperometric technologies are particularly desirable because only a very small sample may be needed to perform the measurement. In electrochemical-based systems, the test strip typically includes a sample chamber that contains reagents, such as an enzyme and a mediator, and electrodes. When the user applies a fluid sample to the sample chamber, the reagents react with the analyte, and the meter applies a voltage to the electrodes to cause a redox reaction. The meter measures the resulting current and calculates the glucose level based on the current. Other systems based on coulometry or voltammetry are also known.

Commercially available biotest strip systems, such as those typically used to measure blood glucose levels, typically have two parts. The first is a reading device, or meter, that contains all the electronics, measurement devices, and power supply necessary to run the test. The second is a test strip portion. The test strip portion typically has some sort of area dedicated to receiving the sample as well as a portion to connect to the meter. For the meter to work properly, it is important that the test strip is inserted in the right orientation. There is a need for methods and systems for ensuring that a correct test strip is inserted into the meter and in a correct orientation.

SUMMARY

Some aspects of the present disclosure provide a system comprising: a diagnostic test strip having a diagnostic end and a meter contacting end, the meter contacting end having at least one identifying feature that distinguishes the meter contacting end from the diagnostic end; a diagnostic meter configured to read information from the meter contacting end of the test strip when the meter contacting end of the test strip is fully inserted in to the meter; and a port in the meter, the port having a gating mechanism configured to identify the meter contacting end and allow the test strip to be fully inserted into the meter only after the gating mechanism identifies the meter contacting end of the test strip as a proper end for insertion.

Some aspects of the present disclosure provide a meter, comprising: a port configured to read information from a meter contacting end of a test strip when the meter contacting end of the test strip is fully inserted in to the meter; and a gating mechanism formed in the port and configured to identify a meter contacting end of a test strip, the gating mechanism being configured to allow the test strip to be fully inserted into the meter only after the gating mechanism identifies the meter contacting end of the test strip as a proper end for insertion.

Some aspects of the present disclosure provide a diagnostic test strip, comprising: diagnostic end configured to receive a sample of a fluid in a sample chamber; and a meter contacting end configured to communicate information about the fluid to a meter upon insertion of the test strip into the meter, the meter contacting end having at least one identifying feature that distinguishes the meter contacting end from the diagnostic end such that the test strip is fully inserted into the meter only after the meter identifies the meter contacting end of the test strip as a proper end for insertion into the meter.

Some aspects of the present disclosure provide a method comprising: placing a sample of a fluid for analysis on a diagnostic test strip, the test strip having a diagnostic end for receiving the sample and a meter contacting end for communicating information to a meter, the meter contacting end having at least one identifying feature that distinguishes the meter contacting end from the diagnostic end; inserting the meter contacting end into a port on the meter, the port having a gating mechanism that identifies the meter contacting end and allows the test strip to be fully inserted into the meter only after the gating mechanism identifies the meter contacting end of the test strip; and reading, with the meter, the information on the diagnostic test strip.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIGS. 17-19 illustrate various embodiments of gating mechanisms.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Figure 1:
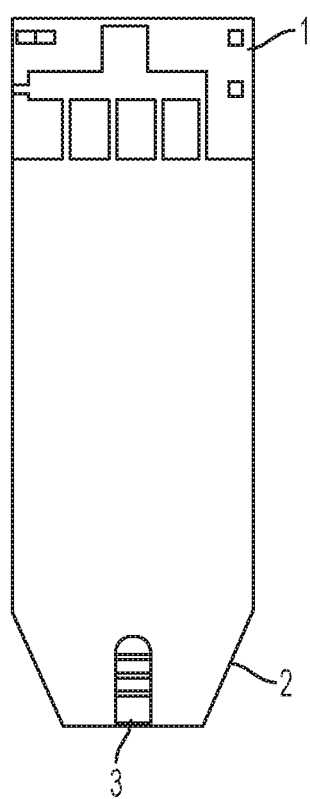
FIG. 1 depicts an embodiment of an exemplary diagnostic test strip.
Figure 2:
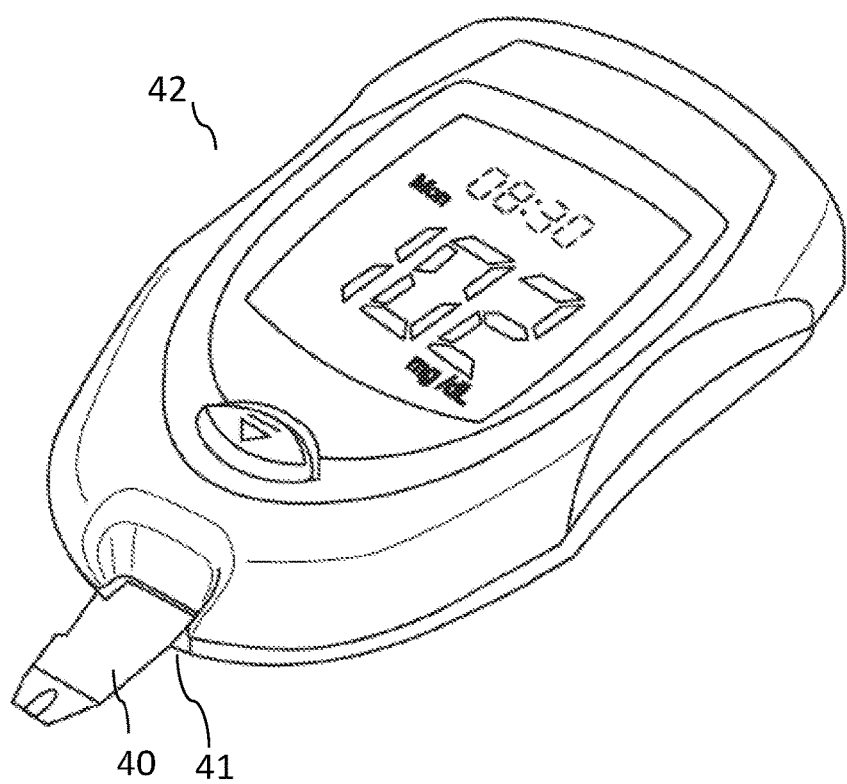
FIG. 2 depicts an embodiment of a test meter with a test strip inserted into the test meter.
Figure 3:
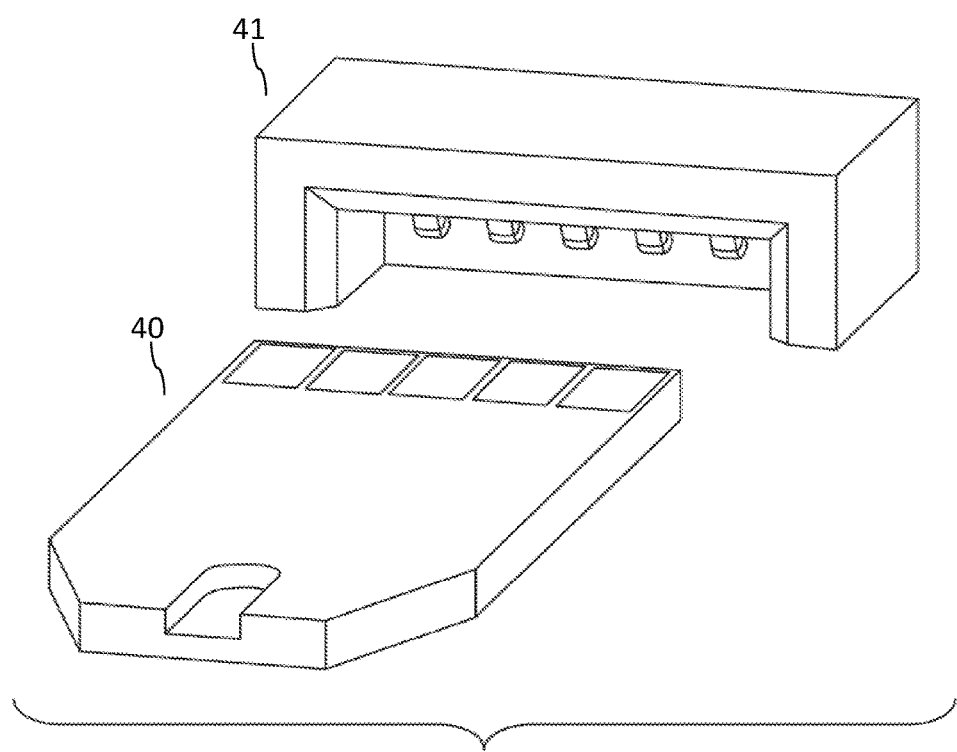
FIG. 3 illustrates a test strip being aligned for insertion into a port of a diagnostic meter.
Figure 4:
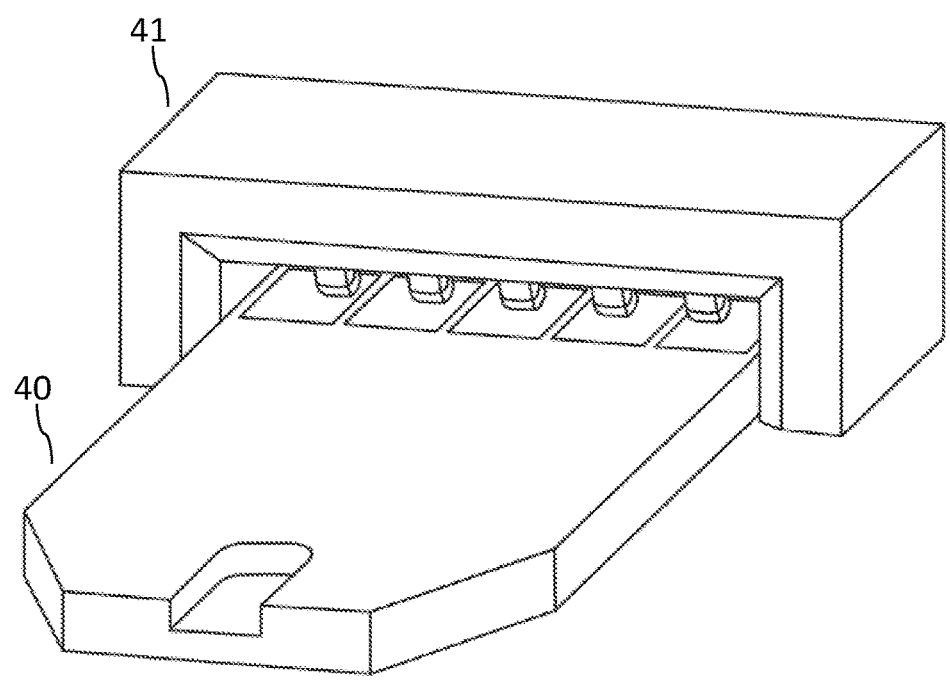
FIG. 4 shows a test strip fully inserted into a port of a diagnostic meter.

According to some embodiments, a system for measuring a constituent of a fluid, for example a body fluid, comprising a diagnostic test strip and a diagnostic meter. As shown in FIG. 1, a test strip may have a diagnostic end 2 which is configured to receive a sample of a fluid in a sample chamber 3, and a meter contacting end 1. In some embodiments, the diagnostic end is beveled. In some embodiments, the meter contacting end is straight edged and configured to communicate information about the fluid to the meter upon insertion of the test strip into the meter. The meter contains all the electronics, measurement devices, and power supply necessary to run the tests. In operation, as shown in FIG. 2, the user inserts a test strip 40 into a port 42 of the meter 42 and, when prompted by the meter, the user applies a blood sample to the test strip. FIG. 3 illustrates the test strip 40 being aligned for insertion into the meter connector port 41. FIG. 4 shows the exemplary diagnostic test strip 40 fully inserted into the connector port 41 of an exemplary meter device. When the test strip is inserted into the meter, electrodes on the test strip electrically connect to the meter so the meter can apply voltage and measure the current between the electrodes in order to determine the blood glucose and hematocrit level in the sample.

The meter contacting end may include one or more features that distinguish it from the diagnostic end of the strip. The port of the meter may be configured to recognize such feature to prevent the user from erroneously inserting the diagnostic end of the strip into the meter or from inserting a test strip not designed for use with the meter. The feature may be a physical feature such as width, thickness or specific shaping. In some embodiments, such features may be used to ensure the proper insertion of the test strip into the port of the test meter.

The port of the meter may comprise a gating mechanism which may be configured to prevent insertion of the strip in to the meter until the strip is recognized or identified as being of the proper shape, size, and/or type. In some embodiments, the port is located on a side of the meter. In some embodiments the port is located on a bottom of the meter. The gating mechanism prevents the strip from being inserted incorrectly into the meter until the gating mechanism recognizes the at least one feature of the meter contacting end that distinguishes the meter contacting end from the diagnostic end. Once the gating mechanism recognizes or identifies the strip as being of the correct shape or size or type, the gating mechanism allows the strip to be fully inserted in to the meter so that information on the strip can be read by the meter, and thereby preventing any sample fluid from contaminating internal components of the meter.

The gating mechanism has a gate which is closed and prevents insertion of the strip until the gating mechanism recognizes the strip, and one or more gate components that are used to specifically identify the meter contacting end of the strip. In some embodiments, the gate components are stops and risers. The stops first make physical contact with the strip, which distributes physical force to the risers and allows the risers to then lift or open the gate after the stops have been contacted. In some embodiments, the gate may stay closed by gravity, and a physical force of the meter contacting end making contact with a stop allows the risers to lift, thereby opening the gate. In some embodiments, the gate may have some additional back force to keep it in place, such as from a spring, hydraulics, electronics or a band or pulley system, gear and lever systems, sled mechanisms or similar mechanisms. In some embodiments, the stops may recognize the meter contacting end of the strip and then via an electronic means allow the gate to open. The gate may be designed to ensure insertion of a correct end of the test strip, insertion of a correct type of test strip, or insertion of both the correct end and correct type of the test strip. Similarly, the gate is designed to prevent insertion of the incorrect end of the test strip, or to prevent insertion of the wrong shape or type of test strip. In some embodiments, the gate may be made of a hydrophobic material to help prevent fluid ingress from a wrongly inserted test strip.

In some embodiments, the gating mechanism comprises a gate that is divided in to two or more sections, each section needing to identify or recognize a feature on the diagnostic strip in order for the gate to fully open. Each section may have its own stops and risers, such that a strip of the wrong shape or size that makes contact with only one set of stops or risers, or not contacting or being recognized by all of the stops or risers, will be prevented from being inserted into the meter. In some embodiments, the gating mechanism requires a specific order of recognition or identification events to occur in order for the gate to open. The order may be determined by a specific shape of a strip making contact with specific gate components in a specific order, like a lock and key mechanism where the strip works as a 'key' with the gate acting as a 'lock.'

Reference will now be made in detail to the exemplary embodiments of the present disclosure, examples of which are illustrated in the accompanying drawings. Wherever possible, the same reference numbers will be used throughout the drawings to refer to the same or like parts. It should be noted that such embodiments are presented solely to illustrate various aspects of the present disclosure and are not intended to limit the present disclosure to the illustrated embodiments.

Referring now to FIGS. 5, 7, 8 and FIG. 9, in some embodiments, a gating mechanism 100 is disposed in a port of a test meter. In some embodiments, the gating mechanism 100 may come down from the top of the port, or up from the floor of the port. In some embodiments the gating mechanism 100 could be located on a side of the port or at any arbitrary angle, depending on the shape of a diagnostic strip being challenged. In some embodiments, the gating mechanism 100 comes down from the top of the port and may uses gravity to hold it in place. In some embodiments, the gate may be bottom mounted and held in a closed configuration via a spring system. The gating mechanism 100 may be configured to challenge the shape or size of an incoming strip and recognizes and allows for insertion of only strips that have the proper shape or size.

Referring now to FIGS. 5-8, the gating mechanism 100 may include a gate 7 and gating components 4, 5. A diagnostic end of the strip 9 may contain a sample of a fluid which preferably not be allowed to be inserted into the meter 200 to protect internal electronic components 8 of the meter 200 from bodily fluids. To this end, for example, the gating components 4, 5 need to contact the test strip for the test strip to be inserted past the gate 100.

Figure 5:
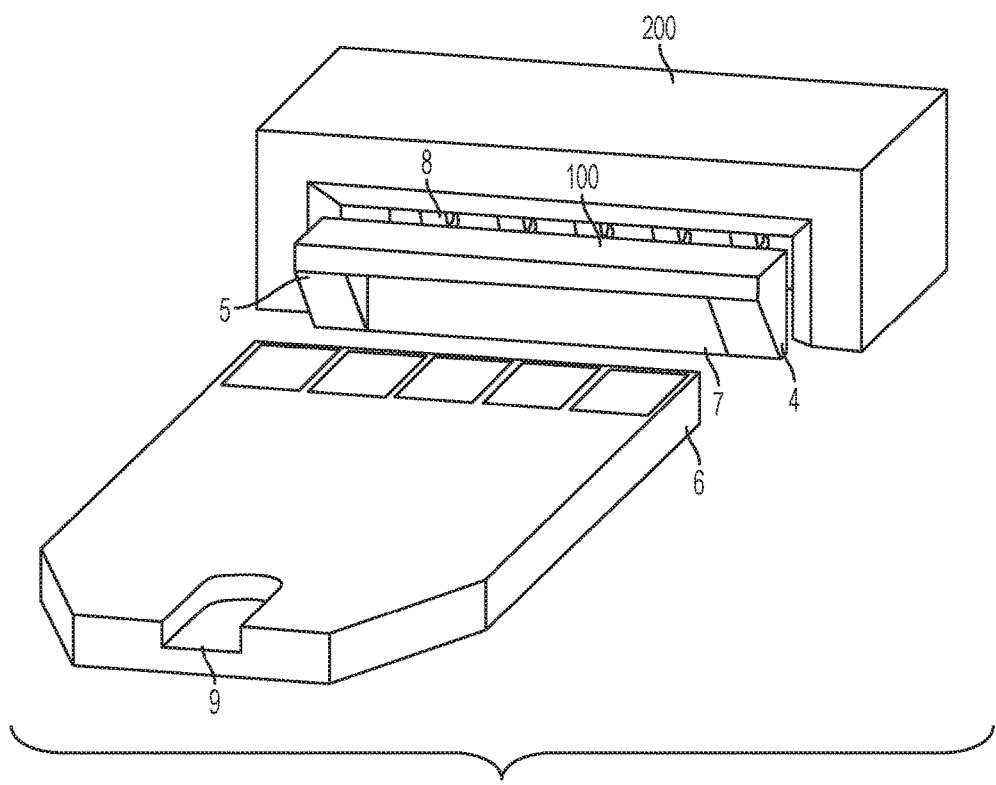
FIGS. 5-8 illustrate an embodiment of a gating mechanism positioned between the entrance and the connector pins of the meter connector.
Figure 6:
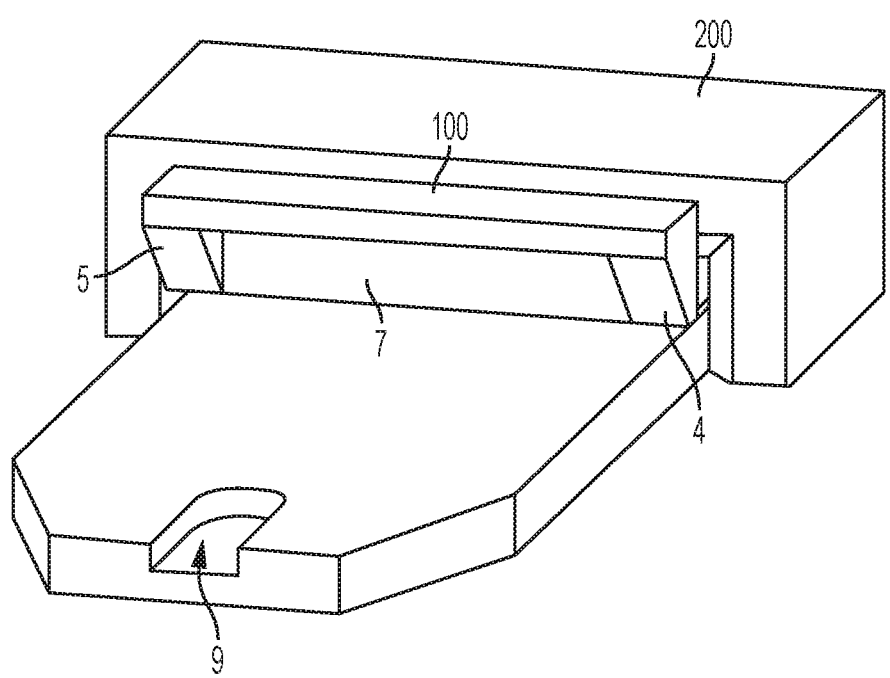
Figure 7:
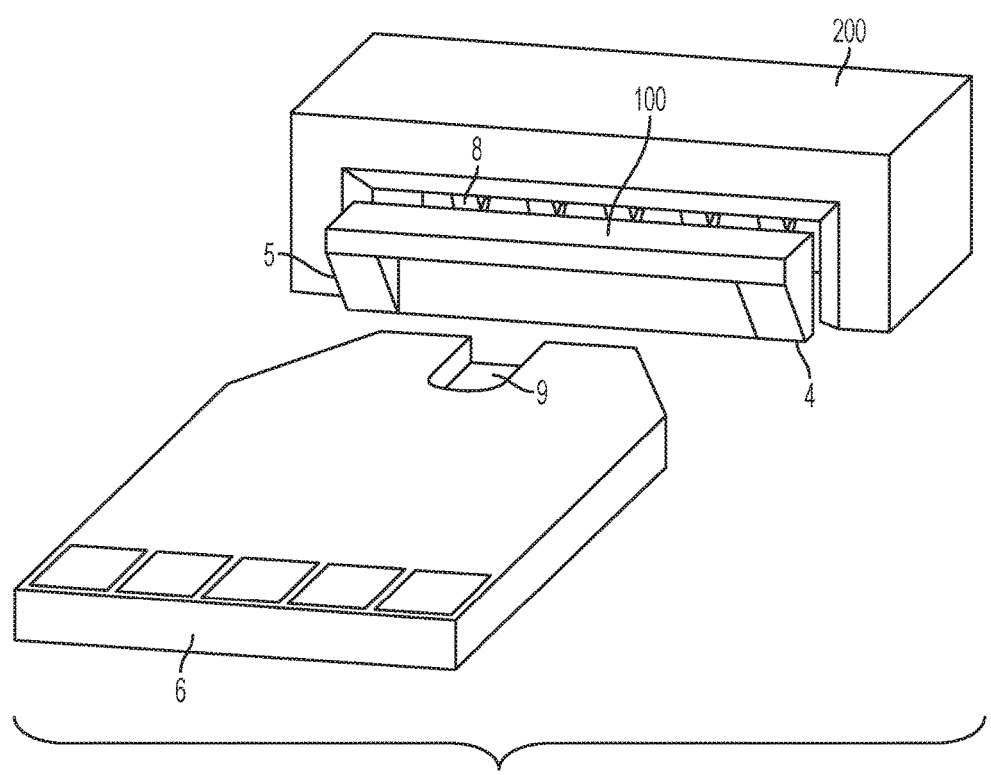
Figure 8:
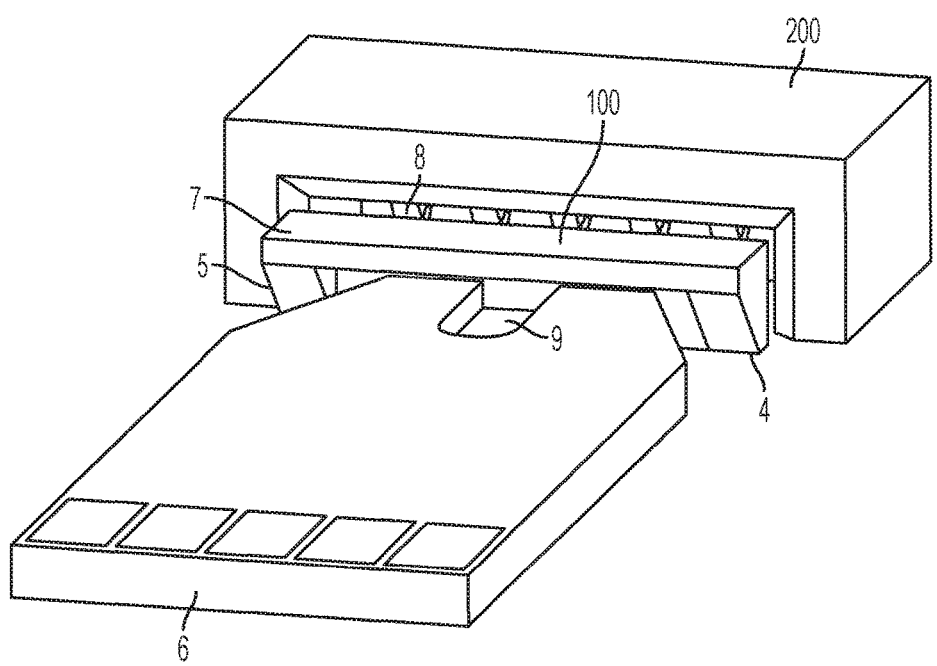

In reference to FIG. 5 and FIG. 6, when the meter contacting end is inserted into the port of the meter, the gating components are contacted and the gating mechanism 100 may allow the test strip to be inserted into the meter so that a diagnostics system in the meter can function as intended. On the other hand, in reference to FIGS. 7-8, a beveled edge at the diagnostic end would hit the center of the gate 100 first, and not touch the gating components 4, 5 (which are inclined planes) at the edges. Since, there is no force applied to the gating components 4, 5, the gating mechanism 100 will remain closed to prevent the wrong end of the test strip to be inserted into the meter. In some embodiments, since the diagnostic end of the strip is improperly shaped so it cannot be inserted into the meter, the gating mechanism can prevent contamination of any interior components of the meter with any sample fluids located on the diagnostic end. Similarly, the gating mechanism may act to prevent the user from using a wrong strip (i.e., a test strip not designed for use with the particular meter).

When the shape of the strip is incorrect and the diagnostic end 9 is beveled, for example, it does not fully contact the gating components 4, 5 of the gate 7, and thus the strip is not allowed to proceed. In some embodiments, the diagnostic end 9 can be any shape where shape differentiation allows the gating components 4, 5 to distinguish the diagnostic end 9 from the meter contacting end 6. The gate functions as a lock, and through shape or size differentiation, only a properly shaped or sized end of the test strip, functioning as a key, can open the lock. Shape or size need not be the only features used to distinguish the meter contacting end 6 from the diagnostic end 9. For example, a strip can be required to create electrical contact between components 4 and 5 before the gate can open.

Figure 9:
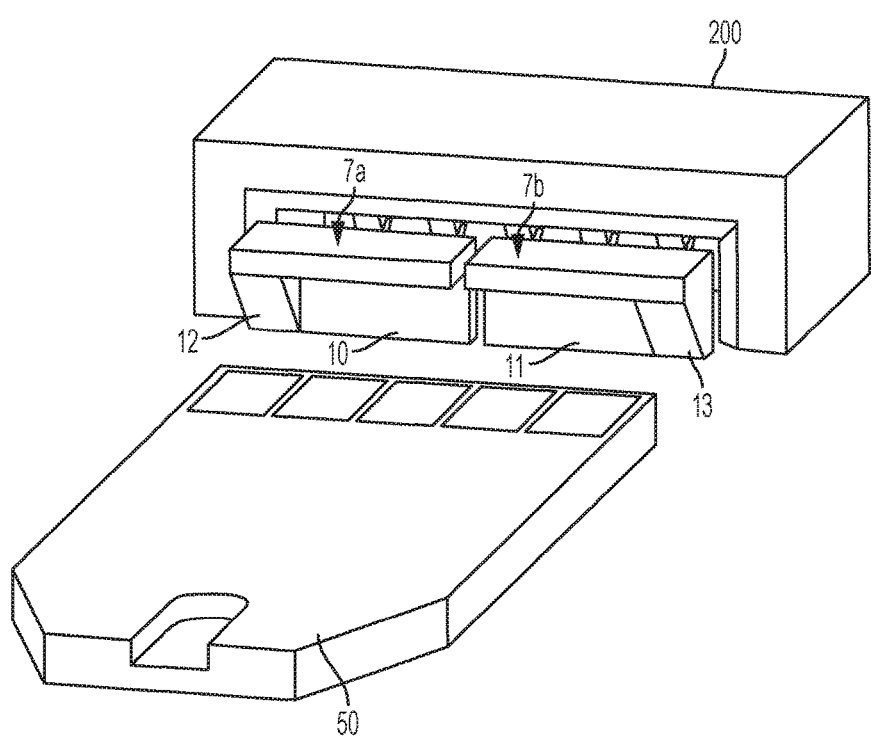
FIGS. 9-11 illustrate an embodiment of a gating mechanism with multiple gate components.
Figure 10:
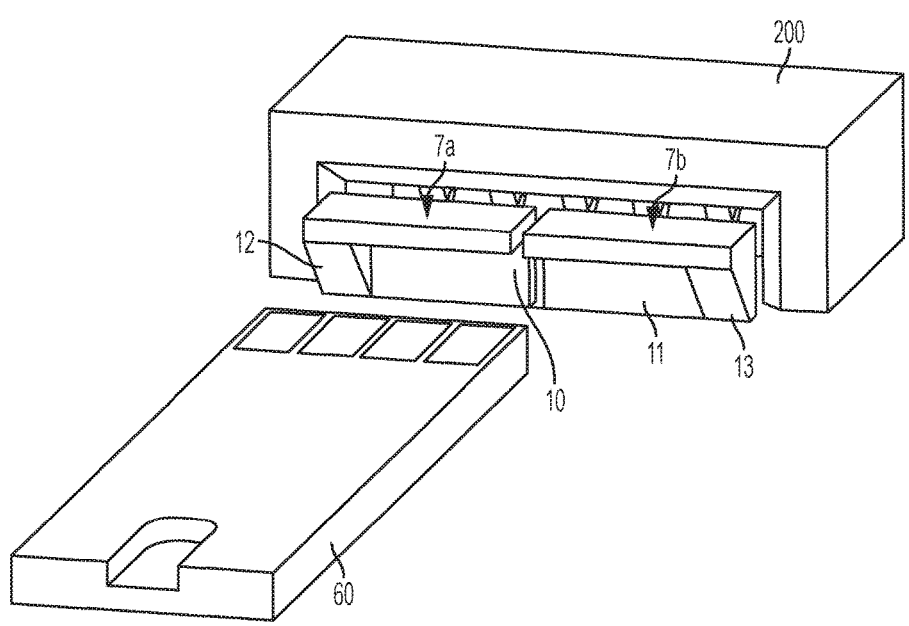
Figure 11:
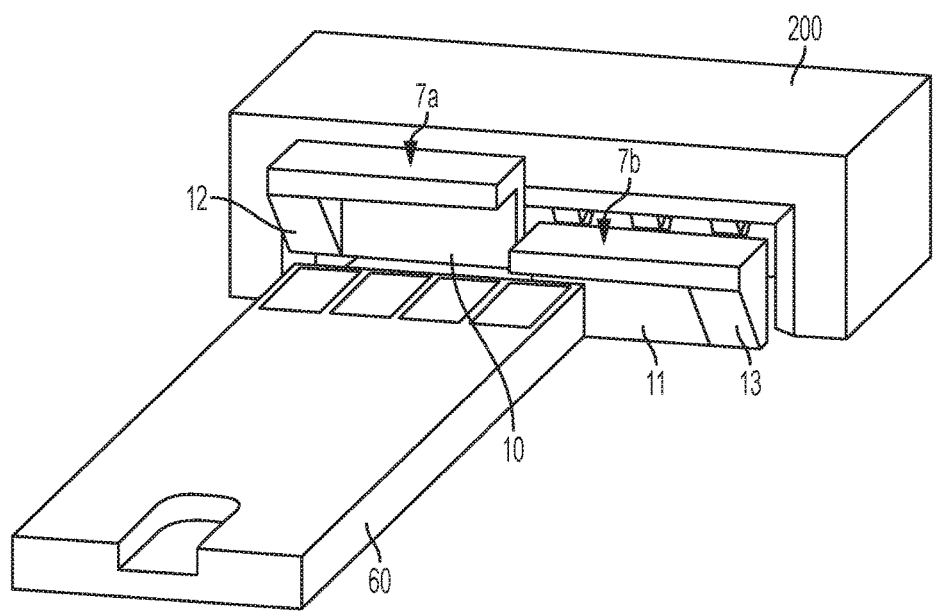

FIGS. 9-11 show an embodiment of a gate 7 having one divider, wherein the divider splits the gate 7 into two regions 7a, 7b, with each region having its own flat sections 10, 11 and gate components (12, 13) (referred to as risers and stops, respectively). In some embodiments, all stops 12, 13 may need to be contacted successfully before the risers 10, 11 are contacted in order for the gate 7 to be opened. In some embodiments, the gate 7 may have more than one divider, splitting the gate into more than two parts or sections. When a strip of proper shape 50 contacts both stops 12, 13, both risers 10, 11 will open and the gate 7 will allow the strip to be inserted into a meter 200, as shown in FIG. 9. When a strip of improper shape 60 is inserted into the port, it will make contact with only one stop 12, which will prevent the entire gate 7 from opening because only one riser 10 will open, as shown in FIGS. 10 and 11.

Figure 12:
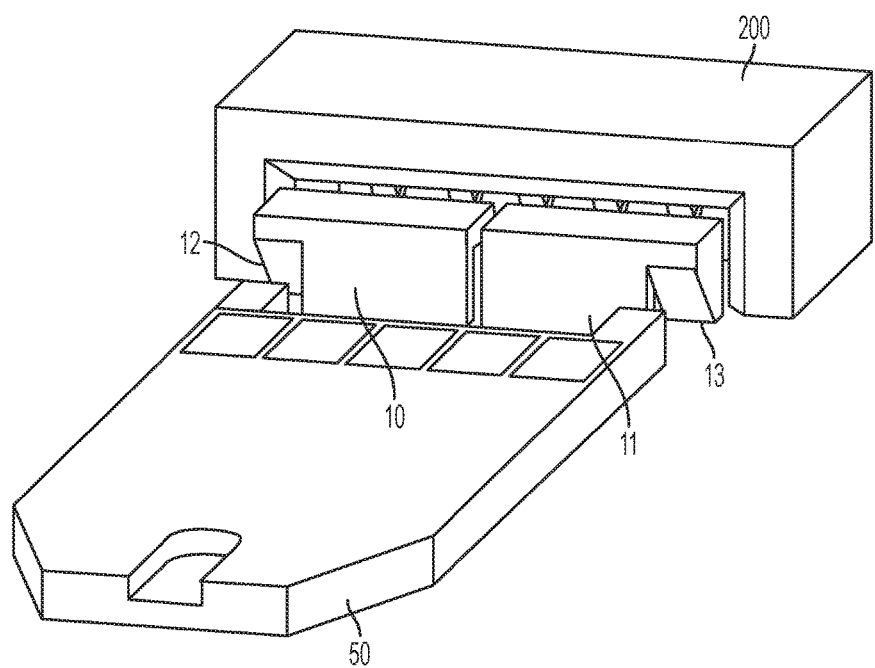
FIGS. 12-13 illustrate an embodiment of a gating mechanism wherein two gate components need to be contacted to allow for insertion of the diagnostic strip, and the diagnostic strip has a particular geometric pattern designed to allow offset of the gate components.
Figure 13:
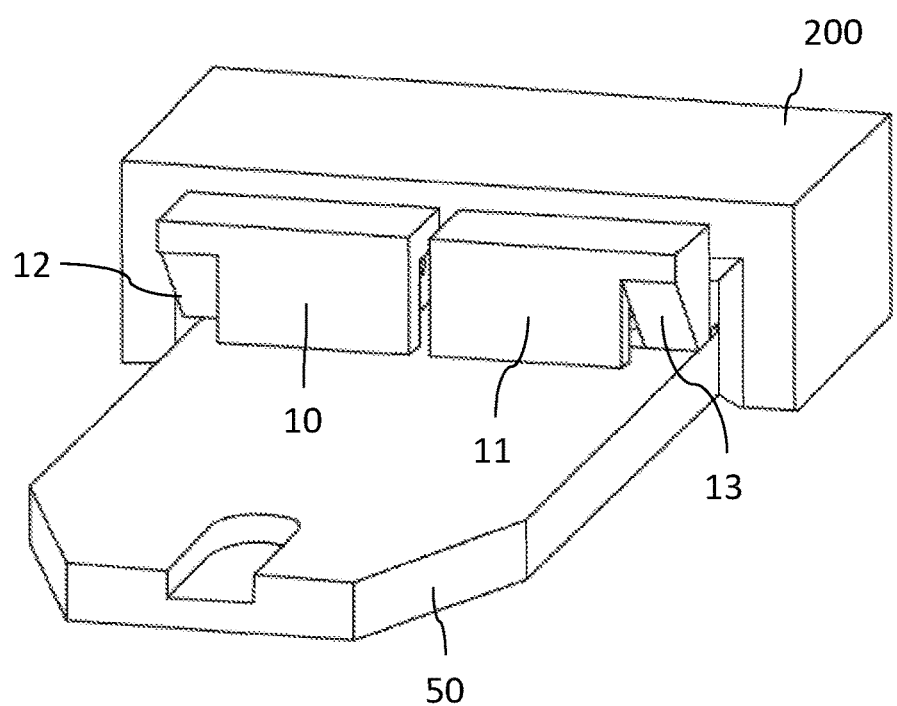

In reference to FIGS. 12-13, the risers do not need to be coplanar with the stops. In some embodiments, the stops can be set back, requiring the meter contacting end of the test strip to have a specific shape. For example, the meter contacting end may be shaped such that certain portions of the strip project forward in order to allow the gate 7 to open. In the exemplary figures, these gates are split, but this is not necessary for this embodiment. A single prong could open a single gate, where the riser is set back from the stop, preventing a flat edged strip from entering. In some embodiments, the risers can be set at different depths relative to the stops and the gate 7 into can be sub-divided into any number of possible portions to create a lock and key mechanism. Each of the subdivisions of the gating mechanism can function analogously to a tumbler in a normal lock system. Only a test strip shape that allows all the subdivisions to rise will be allowed to enter. As can be imagined, the ability to allow insertion of certain strip types not only prevents strip types from different manufacturers from accidentally being used with the meter, it can also allow certain strips from the same manufacturer from being allowed to interface with the meter device.

Figure 14:
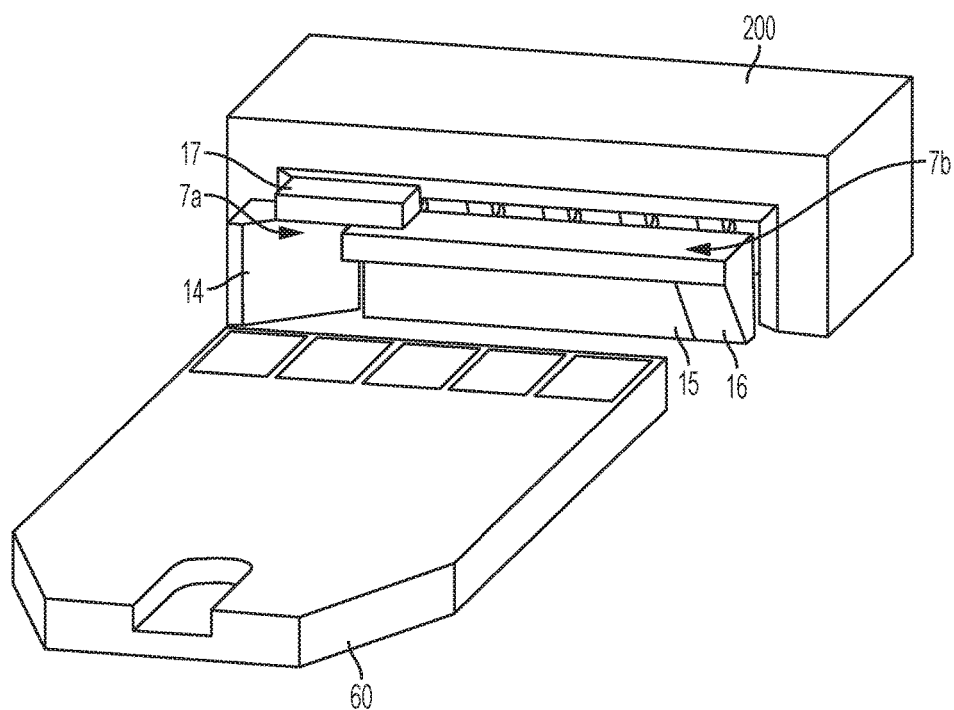
FIGS. 14-16 illustrate an embodiment of a gating mechanism that requires a specific order of contact between the diagnostic strip and the gate components.
Figure 15:
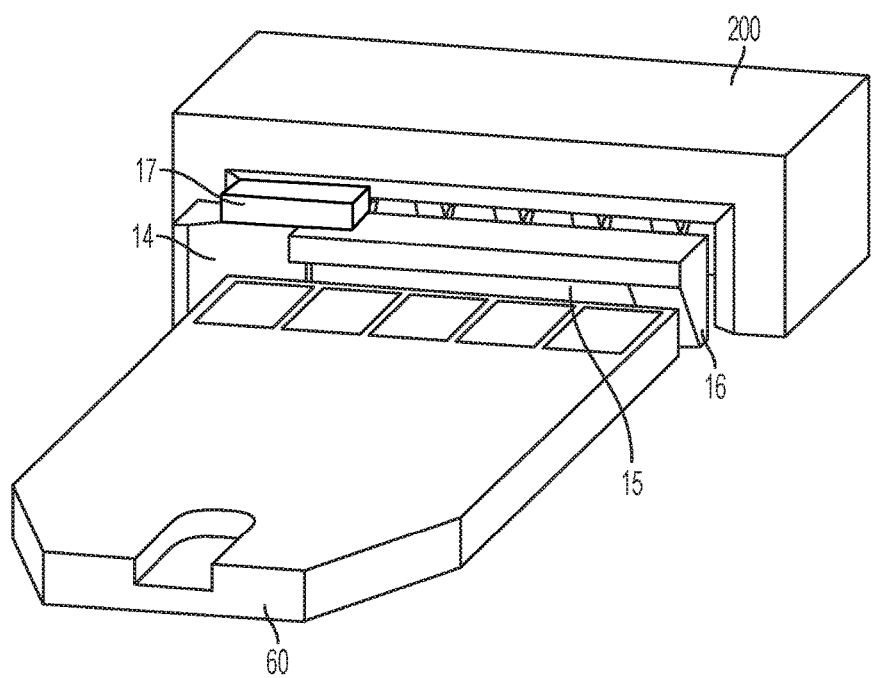
Figure 16:
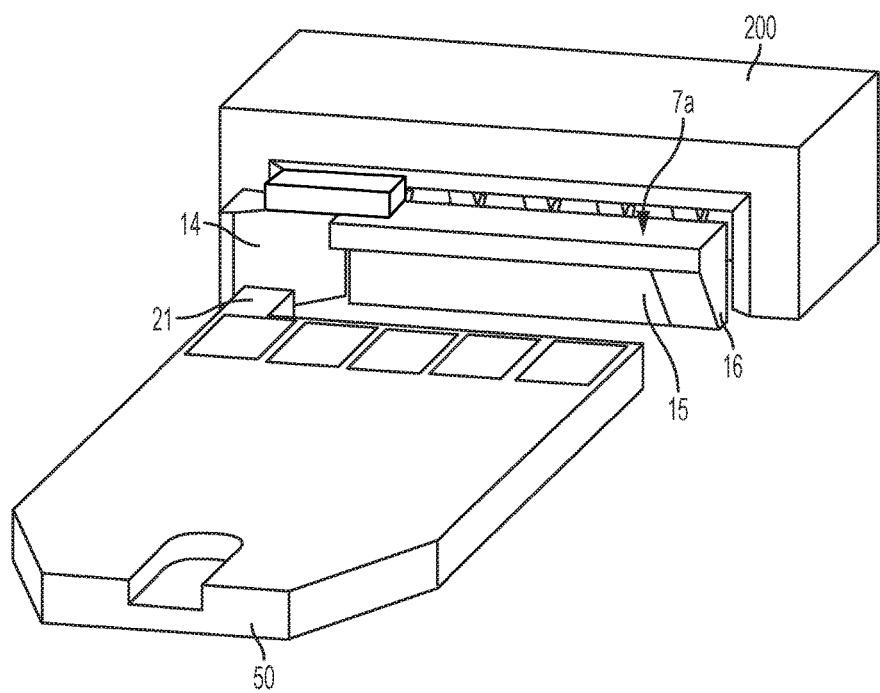

Referring to FIGS. 14-16, in some embodiments the gate 7 can comprise separate portions 7a, 7b. The portion 7a includes a gate portion 14 and a stopper 17, which overlaps with the gate portion 7b. When a test strip of proper shape is inserted (having an extension 21 as shown in FIG. 16) into the port, the gate portion 14 is moved to the side, moving with it the stopper 17. Next, when the test strip hits the stop 16, the raiser 15 can be lifted to allow the test strip to be fully inserted into the port. However, if the gate portion and the stopper 17 are not moved away, the raiser 15 would be able to lift, thus preventing the insertion of the test strip into the port, as shown in FIGS. 14 and 15. In some embodiments, the stop 16 may be absent.

Figure 17:
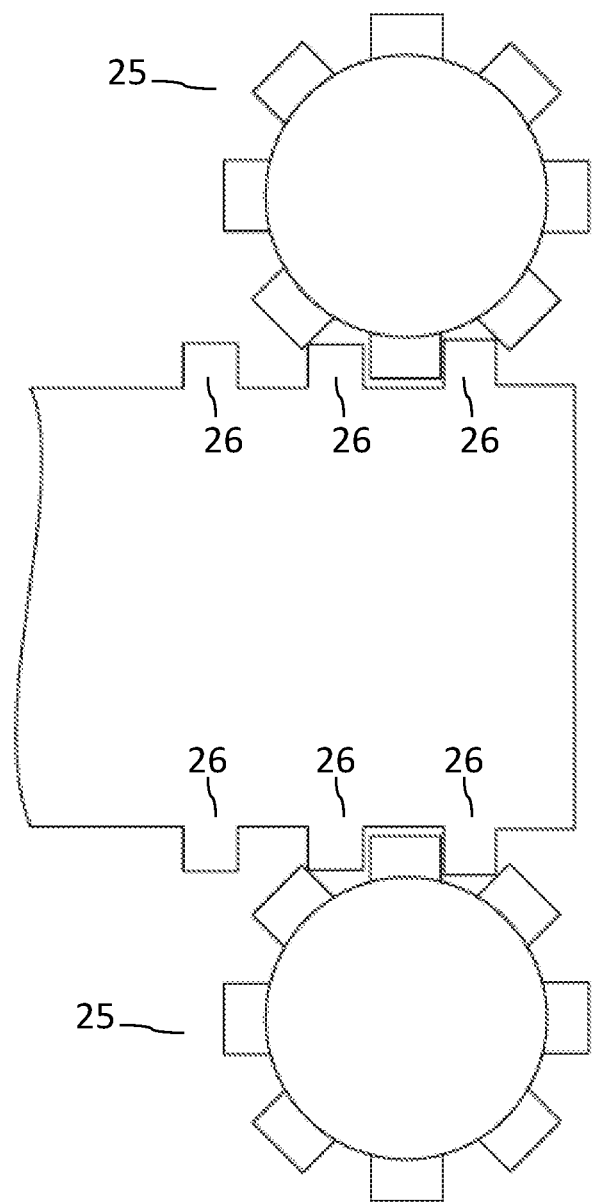

In reference to FIG. 17, in some embodiments, the gating mechanism may include one or more toothed gears 25, which interact with teeth 26 on the strip 50, analogous to a rack and pinion relationship, with the pinion being the gears in the connector, and the rack being the strip itself. Accordingly, the teeth on the strip need to be in correspondence to the toothed gears on the gating mechanism for the test strip to pass through the gating mechanism.

In reference to FIGS. 18A-18B, in some embodiments, instead of or in addition to a gating mechanism, a rocker switch type mechanism 30 may be utilized, where the first contact needs be correctly activated by the incoming strip to move the second portion, which is connected via a lever type mechanism, into revealing a path to the connector.

Figure 19:
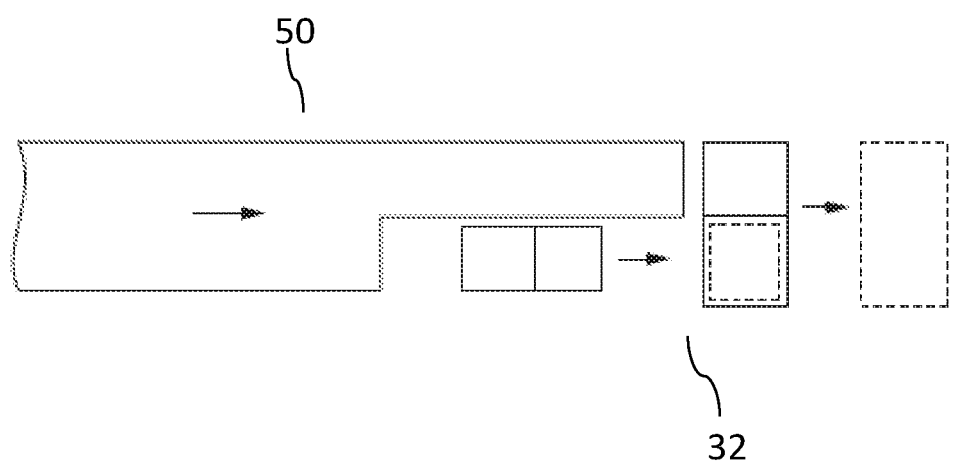

In reference to FIG. 19, in some embodiments, a sled type design 32 can be used, where the gating mechanism is pushed backwards as the strip is inserted. If a strip of the correct shape is inserted, the individual sleds will be pushed back in the correct order and fall into selected holes. If the strip is not of the correct shape, one or more of the sleds will not fall out of the path of the strip.

In some aspects of the present disclosure, there is disclosed a method for measuring or analyzing a constituent of a fluid sample, such as the amount of glucose in blood, with a meter. The method comprises placing a sample of a fluid for analysis on a diagnostic test strip, inserting the test strip into a port on the meter, and reading, with the meter, information carried on the diagnostic test strip. The test strip has a diagnostic end for receiving the sample, with components on the test strip used for analyzing the sample and generating information about the sample, and a meter contacting end for receiving the information from the diagnostic end and communicating the information to the meter. The meter contacting end has at least one identifying feature that distinguishes the meter contacting end from the diagnostic end. The port has a gating mechanism that identifies the at least one identifying feature of the meter contacting end and allows the test strip to be fully inserted into the meter only after the gating mechanism identifies or recognizes the meter contacting end of the test strip.

In an embodiment of the present disclosure, a system for analyzing a constituent of a fluid comprising a diagnostic test strip and a diagnostic meter for reading information about the constituent on the test strip. The diagnostic test strip has a diagnostic end for receiving a sample of the fluid, and a meter contacting end, the meter contacting end having at least one identifying or unique feature that distinguishes the meter contacting end from the diagnostic end. The diagnostic meter is configured to read information from the meter contacting end of the test strip when the meter contacting end of the test strip is fully inserted in to the meter. The diagnostic meter further comprises a port for inserting the diagnostic test strip in to the meter so it can be read, the port having a gating mechanism that identifies the meter contacting end and allows the test strip to be fully inserted into the meter only after the gating mechanism identifies the meter contacting end of the test strip.

In some embodiments, the gating mechanism comprises a gate and at least one gate component which identifies the meter contacting end of the diagnostic test strip as the correct end for insertion into the meter. In some embodiments, the gating mechanism comprises more than one gate component which identifies the meter contacting end of the diagnostic test strip. In some embodiments, the gating mechanism allows the test strip to be fully inserted into the port by opening the gate only after all of the gate components identify and/or contact the meter contacting end in a specific, pre-set order.

In some embodiments, a method comprises (a) placing a sample of a fluid for analysis on a diagnostic test strip, the test strip having a diagnostic end for receiving the sample and a meter contacting end for communicating information to a meter, the meter contacting end having at least one identifying feature that distinguishes the meter contacting end from the diagnostic end; (b) inserting the meter contacting end into a port on the meter, the port having a gating mechanism that identifies the meter contacting end and allows the test strip to be fully inserted into the meter only after the gating mechanism identifies the meter contacting end of the test strip; and (c) reading, with the meter, the information on the diagnostic test strip.

In some embodiments, the gating mechanism may include one or more toothed gears, which interact with teeth on the strip, analogous to a rack and pinion relationship, with the pinion being the gears in the connector, and the rack being the strip itself.

In some embodiments, instead of a gate, there is a rocker switch type mechanism, where the first contact must be correctly activated by the incoming strip to move the second portion, which is connected via a lever type mechanism, into revealing a path to the connector.

In some embodiments, a sled type design can be used, similar to the gate system in other embodiments, but where the gating mechanism is pushed backwards as the strip is inserted. If a strip of the correct shape is inserted, the individual sleds will be pushed back in the correct order and fall into selected holes. If the strip is not of the correct shape, one or more of the sleds will not fall out of the path of the strip.

Whereas many alterations and modifications of the present disclosure will no doubt become apparent to a person of ordinary skill in the art after having read the foregoing description, it is to be understood that the particular embodiments shown and described by way of illustration are in no way intended to be considered limiting. Further, the disclosure has been described with reference to particular preferred embodiments, but variations within the spirit and scope of the disclosure will occur to those skilled in the art. It is noted that the foregoing examples have been provided merely for the purpose of explanation and are in no way to be construed as limiting of the present disclosure. While the present disclosure has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present disclosure in its aspects. Although the present disclosure has been described herein with reference to particular means, materials and embodiments, the present disclosure is not intended to be limited to the particulars disclosed herein; rather, the present disclosure extends to all functionally equivalent structures, methods and uses, such as are within the scope of the appended claims.

What is claimed is:

1. A system comprising:
a diagnostic test strip having a diagnostic end and a meter contacting end, the meter contacting end having at least one identifying feature that distinguishes the meter contacting end from the diagnostic end;
a diagnostic meter configured to read information from the meter contacting end of the test strip when the meter contacting end of the test strip is fully inserted into the meter; and
a port in the meter, the port having a gating mechanism configured to identify the meter contacting end and allow the test strip to be fully inserted into the meter only after the gating mechanism identifies the meter contacting end of the test strip as a proper end for insertion, wherein the gating mechanism includes one or more gates configured to be closed to prevent insertion of the test strip until the gating mechanism recognizes the strip.

2. The system of claim 1, wherein the gating mechanism comprises a plurality of gate components which identify the meter contacting end of the diagnostic test strip.

3. The system of claim 2, wherein the gating mechanism allows the test strip to be fully inserted into the port after the plurality of gate components contact the meter contacting end in a specific, pre-set order.

4. The system of claim 1, wherein the at least one identifying feature comprises one or more of width, thickness or a pre-determined shaping.

5. The system of claim 1, wherein the gating mechanism comprises one or more inclined planes and the test strip is shaped and sized to contact each of the one or more inclined planes in a predetermined order to open the gating mechanism.

6. The system of claim 1, wherein the gating mechanism comprises a first gate and a second gate and wherein the first gate includes a stopper overlapping the second gate such that the stopper can prevent the second gate from opening.

7. The system of claim 1, wherein the gating mechanism comprises two or more gates, wherein each of the gates includes at least one stop and at least one riser, the at least one stop is configured to make physical contact with the meter contacting end of the test strip to allow the at least one riser to lift and open the gating mechanism.

8. A meter comprising:
a port configured to read information from a meter contacting end of a test strip when the meter contacting end of the test strip is fully inserted in to the meter; and a gating mechanism formed in the port and configured to identify a meter contacting end of the test strip, the gating mechanism being configured to allow the test strip to be fully inserted into the meter only after the gating mechanism identifies the meter contacting end of the test strip as a proper end for insertion, wherein the gating mechanism includes one or more gates configured to be closed to prevent insertion of the test strip until the gating mechanism recognizes the strip.

9. The meter of claim 8, wherein the gating mechanism comprises a first gate and a second gate and wherein the first gate includes a stopper overlapping the second gate such that the stopper can prevent the second gate from opening.

10. The meter of claim 8, wherein the gating mechanism comprises a plurality of gate components which identify the meter contacting end of the diagnostic test strip.

11. The meter of claim 10, wherein the gating mechanism allows the test strip to be fully inserted into the port after the plurality of gate components contact the meter contacting end in a specific, pre-set order.

12. The meter of claim 8, wherein the at least one identifying feature comprises one or more of width, thickness or a pre-determined shaping.

13. The meter of claim 8, wherein the gating mechanism comprises one or more inclined planes and the test strip is shaped and sized to contact each of the one or more inclined planes in a predetermined order to open the gating mechanism.

14. The meter of claim 8, wherein the gating mechanism comprises two or more gates, wherein each of the gates includes at least one stop and at least one riser, the at least one stop is configured to make physical contact with the meter contacting end of the test strip to allow the at least one riser to lift and open the gating mechanism.

15. A method comprising:
    placing a sample of a fluid for analysis on a diagnostic test strip, the test strip having a diagnostic end for receiving the sample and a meter contacting end for communicating information to a meter, the meter contacting end having at least one identifying feature that distinguishes the meter contacting end from the diagnostic end;
    inserting the meter contacting end into a port of the meter, the port having a gating mechanism that identifies the meter contacting end and allows the test strip to be fully inserted into the meter only after the gating mechanism identifies the meter contacting end of the test strip, wherein the gating mechanism includes one or more gates configured to be closed to prevent insertion of the test strip until the gating mechanism recognizes the strip; and
    causing the meter to read the information on the diagnostic test strip.

16. The method of claim 15, wherein the gating mechanism comprises a plurality of gate components which identify the meter contacting end of the diagnostic test strip.

17. The method of claim 16, wherein the gating mechanism allows the test strip to be fully inserted into the port after the plurality of gate components contact the meter contacting end in a specific, pre-set order.

18. The method of claim 15, wherein the at least one identifying feature comprises one or more of width, thickness or a pre-determined shaping.

19. The method of claim 15, wherein the gating mechanism comprises one or more inclined planes and the test strip is shaped and sized to contact each of the one or more inclined planes in a predetermined order to open the gating mechanism.

20. The method of claim 15, wherein the gating mechanism comprises two or more gates, wherein each of the gates includes at least one stop and at least one riser, the at least one stop is configured to make physical contact with the meter contacting end of the test strip to allow the at least one riser to lift and open the gating mechanism.

21. The method of claim 15, wherein the gating mechanism comprises a first gate and a second gate and wherein the first gate includes a stopper overlapping the second gate such that the stopper can prevent the second gate from opening.

* * * * *